United States Patent
Ohtsuka et al.

(10) Patent No.: US 6,933,413 B2
(45) Date of Patent: Aug. 23, 2005

(54) PROCESSES FOR PREPARATION OF HEXAFLUOROACETONE AND ITS HYDRATE

(75) Inventors: Tatsuya Ohtsuka, Settsu (JP); Yoshihiro Yamamoto, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/482,410

(22) PCT Filed: Jul. 2, 2002

(86) PCT No.: PCT/JP02/06672

§ 371 (c)(1),
(2), (4) Date: Jan. 9, 2004

(87) PCT Pub. No.: WO03/008366

PCT Pub. Date: Jan. 30, 2003

(65) Prior Publication Data

US 2004/0186322 A1 Sep. 23, 2004

(30) Foreign Application Priority Data

Jul. 19, 2001 (JP) ....................... 2001-219170

(51) Int. Cl.⁷ ............................................. C07C 45/00
(52) U.S. Cl. ...................... 568/384; 568/386; 568/391; 568/393; 568/411
(58) Field of Search ................................. 568/384, 386, 568/391, 393, 411

(56) References Cited

U.S. PATENT DOCUMENTS

| 3,321,515 A | 5/1967 | Moore et al. | |
| 3,544,633 A | 12/1970 | Yodis et al. | 260/593 |
| 4,386,223 A | 5/1983 | Kawai et al. | 568/411 |
| 4,544,722 A | 10/1985 | Giddings et al. | 568/264 |
| 4,544,772 A | 10/1985 | Sawai et al. | 568/411 |

FOREIGN PATENT DOCUMENTS

| JP | 53-25512 | 3/1978 |
| JP | 58-62130 | 4/1983 |
| JP | 58-62131 | 4/1983 |
| JP | 59-204142 | 11/1984 |
| JP | 04-10456 | 1/1992 |

*Primary Examiner*—Samuel Barts
*Assistant Examiner*—Sikarl A. Witherspoon
(74) *Attorney, Agent, or Firm*—Armstrong, Kratz, Quintos, Hanson & Brooks, LLP

(57) ABSTRACT

The present invention provides a process for the preparation of hexafluoroacetone characterized by bringing hexafluoro-1,2-epoxypropane into contact with at least one catalyst selected from the group consisting of titanium oxide catalysts and fluorinated titanium oxide catalysts to isomerize hexafluoro-1,2-epoxypropane; and a process for the preparation of hexafluoroacetone hydrate characterized by absorbing the hexafluoroacetone prepared by the above process into water to produce crude hexafluoroacetone hydrate, neutralizing the crude hexafluoroacetone hydrate with an alkali, and distilling the resulting mixture. According to the invention, high-purity hexafluoroacetone can be obtained by isomerization of hexafluoro-1,2-epoxypropane with little formation of by-products, and substantially acid-free high-purity hexafluoroacetone hydrate can also be obtained.

3 Claims, No Drawings

PROCESSES FOR PREPARATION OF HEXAFLUOROACETONE AND ITS HYDRATE

TECHNICAL FIELD

The present invention relates to a process for preparing hexafluoroacetone and a process for preparing hexafluoroacetone hydrate.

BACKGROUND ART

Hexafluoroacetone and hexafluoroacetone hydrate are useful as intermediates in the synthesis of various fluorine-containing compounds. For instance, hexafluoroacetone is reacted with various aromatic compounds, and the resulting products are used as a crosslinking agent for rubber or as a monomer for fluorine-containing polyimides. Hexafluoroacetone hydrate is reduced to hexafluoroisopropanol by hydrogen reduction and is used as a material for anesthetics.

For the preparation of hexafluoroacetone, various methods have been known so far, and methods such as the isomerization of hexafluoro-1,2-epoxypropane have been proposed. For example, U.S. Pat. No. 3,321,515 discloses a method of isomerizing hexafluoro-1,2-epoxypropane in the presence of a catalyst such as $Al_2O_3$, $TiO_2$, $WO_2$, $AlCl_3$, $AlBr_3$, $SnCl_4$, $VoCl_3$, $TiCl_4$, $FeCl_3$, $CuCl_2$, $ZrOCl_2$ and so on. However, in the method using these catalysts, conversion of the starting material, hexafluoro-1,2-epoxypropane, is not satisfactory, resulting in a low yield of hexafluoroacetone. Improvement in this respect has been strongly desired.

In attempts to increase the conversion of hexafluoro-1,2-epoxypropane, Japanese unexamined patent publication No. 1978-25512 discloses a method of using a fluorinated alumina catalyst; and Japanese unexamined patent publications No. 1983-62130, No. 1983-62131, etc. describe methods of using as a catalyst, fluorinated metal oxides principally comprising fluorinated chromium oxide, fluorinated aluminum oxide, or the like. Although the use of these catalysts enhances the conversion of hexafluoro-1,2-epoxypropane and makes the yield of hexafluoroacetone comparatively high, pentafluoropropionyl fluoride, trifluoroacetyl fluoride, or the like is formed as a by-product. Of these by-products, pentafluoropropionyl fluoride is especially problematic, because the boiling point of pentafluoropropionyl fluoride is very close to that of hexafluoroacetone. Thus, it is difficult to separate pentafluoropropionyl fluoride from hexafluoroacetone by distillation.

As disclosed in Japanese unexamined patent publications No. 1984-204142, No. 1992-10456, etc., hexafluoroacetone is absorbed into water to produce its hydrate, which is then reduced by hydrogenation in the presence of a catalyst at about 70° C. to about 75° C. to be converted into hexafluoroisopropyl alcohol.

However, the obtained hexafluoroacetone usually contains about 2% pentafluoropropionyl fluoride. When the hexafluoroacetone containing such impurities is dissolved in water for hydration, pentafluoropropionyl fluoride is decomposed to produce the corresponding carboxylic acid and hydrogen fluoride (HF), resulting in a solution highly corrosive to metal.

When this solution is used as a material for the preparation of hexafluoroisopropyl alcohol, heavy corrosion of the reactor and deterioration of the catalyst tend to occur. Therefore, acid-free hexafluoroacetone hydrate is strongly desired.

In an attempt to produce acid-free hexafluoroacetone, U.S. Pat. No. 3,544,633, for example, discloses a method of feeding acid-containing hexafluoroacetone to a weakly alkaline salt such as sodium carbonate etc. at a temperature below 160° C. In this method, however, neutralizing acid fluoride such as pentafluoropropionyl fluoride etc. is not easy. Further, the method shows extremely poor workability in operations such as removing the salts formed by the neutralization of HF.

DISCLOSURE OF THE INVENTION

A principal object of the present invention is to provide a process for the preparation of hexafluoroacetone by isomerizing hexafluoro-1,2-epoxypropane, wherein high-purity hexafluoroacetone can be produced with little formation of by-products such as pentafluoropropionyl fluoride, trifluoroacetyl fluoride and the like.

Another object of the present invention is to provide a process that can produce substantially acid-free high-purity hexafluoroacetone hydrate.

The present inventors conducted extensive research in order to solve the above-mentioned problems. As a consequence, it was found that when at least one catalyst selected from the group consisting of titanium oxides and fluorinated titanium oxides is used as the catalyst for the isomerization of hexafluoro-1,2-epoxypropane, hexafluoroacetone can be produced with extremely high selectivity. It was also found that when the produced hexafluoroacetone is hydrated and then simply subjected to neutralization with an alkali and subsequent distillation, extremely high-purity hexafluoroacetone hydrate can be obtained. Based on these findings, the present invention has been accomplished.

The present invention provides a process for preparing hexafluoroacetone and a process for preparing hexafluoroacetone hydrate as follows:

1. A process for preparing hexafluoroacetone which comprises bringing hexafluoro-1,2-epoxypropane into contact with at least one catalyst selected from the group consisting of titanium oxide catalysts and fluorinated titanium oxide catalysts to isomerize hexafluoro-1,2-epoxypropane.

2. A process for preparing hexafluoroacetone hydrate which comprises:
   bringing hexafluoro-1,2-epoxypropane into contact with at least one catalyst selected from the group consisting of titanium oxide catalysts and fluorinated titanium oxide catalysts to give hexafluoroacetone by isomerization,
   absorbing the produced hexafluoroacetone into water to give crude hexafluoroacetone hydrate,
   neutralizing the crude hexafluoroacetone hydrate with an alkali, and
   distilling the resulting mixture.

3. The process for preparing hexafluoroacetone hydrate according to item 2, wherein the alkali is at least one compound selected from the group consisting of alkali metal carbonates, alkali metal hydrogencarbonates, alkali metal hydrogenphosphates, alkali metal borates, alkali metal sulfites, alkali metal hydroxides, alkaline earth metal carbonates, alkaline earth metal hydrogencarbonates, alkaline earth metal hydrogenphosphates, alkaline earth metal borates, alkaline earth metal sulfites, and alkaline earth metal hydroxides.

The present invention provides a process for preparing hexafluoroacetone, wherein hexafluoro-1,2-epoxypropane as a starting material is isomerized by contact with at least one catalyst selected from the group consisting of titanium oxide catalysts and fluorinated titanium oxide catalysts. The process of the invention is described in detail below.

Catalyst

Usable titanium oxide catalysts are those which comprise titanium dioxide as a principal component, and may optionally contain one or more nonvolatile substance(s) such as other metal oxides, hydroxides, sulfates, halides, oxyhalides, nitrates, phosphates, sulfides or the like. The titanium oxide catalyst preferably contains about 70 wt. % or more titanium dioxide.

Especially favorable as the titanium dioxide is anatase titanium dioxide, which preferably has a specific surface area of about 5 to about 100 m$^2$/g and a pore volume of about 0.2 to about 0.4 ml/g. It is also desired that the catalyst be spherically shaped. Usable titanium dioxides include those commercially available under the trade names of "CS-200", "CS-300", "CS-950" and the like (products of Sakai Chemical Industry Co., Ltd.).

The titanium oxide catalyst can show higher activity by fluorination. Therefore, the titanium oxide catalyst may be fluorinated, before the catalytic reaction for isomerizing hexafluoro-1,2-epoxypropane, to be used as a fluorinated titanium oxide catalyst.

Examples of agents used for fluorinating the titanium oxide catalyst are inorganic fluorinating agents such as hydrogen fluoride (HF), etc; organic fluorinating agents such as fluorocarbon compounds including hexafluoropropene, etc; and so on.

A suitable method for fluorinating the titanium oxide catalyst is, for example, to feed anhydrous HF to the catalyst at atmospheric pressure at a temperature of about room temperature to about 300° C.

The fluorinated titanium oxide catalyst can be deemed to be a mixture of TiOF$_2$ and TiO$_2$, and the fluorine content in the catalyst is preferably about 0.1 to about 38 mass %, and more preferably about 2.5 to about 10 mass %, based on the total amount of the catalyst.

Used in the process of the present invention is at least one catalyst selected from the group consisting of the above-mentioned titanium oxide catalysts and fluorinated titanium oxide catalysts. The titanium oxide catalyst, when used in the process of the invention, is gradually fluorinated with hexafluoro-1,2-epoxypropane to be converted into the fluorinated titanium oxide catalyst.

It is preferable for the process of the invention to use a catalyst previously dried by heating in a stream of inert gas such as N$_2$, etc. The predrying treatment is not necessarily required; however, when the catalyst is not predried, an induction period of several hours is usually needed for the reaction to start.

Although the drying temperature is not restricted, heating at high temperature can reduce the drying treatment time. Usually, the catalyst is dried by heating at about 100° C. to about 300° C. for about 0.5 to about 3 hours.

Preparation of Hexafluoroacetone

The present invention uses hexafluoro-1,2-epoxypropane, which is a known compound, as a starting material.

In the process of the invention, the starting material, hexafluoro-1,2-epoxypropane, is isomerized by being brought into contact with at least one catalyst selected from the group consisting of the above-mentioned titanium oxide catalysts and fluorinated titanium oxide catalysts, to produce hexafluoroacetone with high selectivity.

The method of contacting hexafluoro-1,2-epoxypropane with the catalyst(s) is not restricted, and various known reactors such as tubular reactors, fluidized bed reactors and the like may be used.

The preferable isomerization temperature is usually about 0° C. to about 300° C.; particularly about 150° C. to about 300° C. when titanium oxide catalysts are used; and particularly about room temperature to about 150° C. when fluorinated titanium oxide catalysts are used.

The reaction pressure is not restricted, and the reaction may be carried out at ordinary pressure or under increased pressure. Usually, the reaction pressure is about 0.1 to about 50 atmospheres (about 10 kPa to about 5 MPa), and preferably about atmospheric pressure to about 6 atmospheres (about 100 kPa to about 600 kPa).

The contact time in the reactor, which is not limited, is usually about 0.1 to about 1,000 seconds.

The process of the present invention can suppress side reactions by using the above-mentioned specific catalysts and produce hexafluoroacetone with high selectivity.

Preparation of Hexafluoroacetone Hydrate

Hexafluoroacetone obtained by the above-mentioned isomerization can be converted into crude hexafluoroacetone hydrate by absorbing the hexafluoroacetone into water without purification such as liquefaction and distillation.

Hexafluoroacetone hydrate is represented by the following general formula:

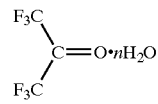

In the preparation of hexafluoroacetone hydrate of the invention, "n" in the above formula is preferably in the range of about 2.5 to about 5. It is known that when "n" is 3, hexafluoroacetone hydrate forms a constant-boiling composition having a boiling point of about 106° C. However, when "n" is too small, solid monohydrate is produced, making distillation difficult; and when "n" is too large, although distillation can be performed, the rate of reduction of the hydrate to hexafluoroisopropyl alcohol is slowed, resulting in decreased productivity.

Hexafluoroacetone hydrate having "n" in the above formula in the range of about 2.5 to about 5 can be prepared, for example, by mixing about 1.8 to about 3.7 parts by weight of hexafluoroacetone gas with 1 part by weight of water and absorbing the hexafluoroacetone gas into the water. Although a countercurrent contact column, autoclave, etc. can be used for mixing hexafluoroacetone gas with water and absorbing the gas into the water, the equipment to be used is not limited to these.

Subsequently, the produced crude hexafluoroacetone hydrate can be purified by neutralization with an alkali and subsequent distillation. The alkali to be used is not restricted. For example, alkali metal or alkaline earth metal carbonates, alkali metal or alkaline earth metal hydrogencarbonates, alkali metal or alkaline earth metal hydrogenphosphates, alkali metal or alkaline earth metal borates, alkali metal or alkaline earth metal sulfites, alkali metal or alkaline earth metal hydroxides, and the like can be used singly or in combination of two or more. Especially preferable are Na$_2$CO$_3$, NaHCO$_3$, K$_2$CO$_3$, KHCO$_3$, CaCO$_3$, Na$_2$SO$_3$, NaBO$_2$, Na$_2$B$_4$O$_7$, Na$_4$P$_2$O$_7$, NaHPO$_4$, etc. These hardly decompose hexafluoroacetone even when used in large amounts, thus facilitating control of the amount to be added.

The amount of alkali to be used is not limited. The alkali is used preferably in an amount of about 1 to about 2 equivalent weight of alkali, and more preferably in an amount of about 1.1 to about 1.3 equivalent weight of alkali, per equivalent weight of acid in the crude hexafluoroacetone hydrate. When using a weak alkali such as carbonate etc., even in large excess, hexafluoroacetone is hardly decomposed. Economically, however, it is appropriate to use about 1 to about 2 wt. % of alkali, relative to the weight of hexafluoroacetone hydrate.

After neutralization, hexafluoroacetone hydrate is separated by distillation. The conditions for distillation are not limited, and usually, distillation can be carried out at atmospheric pressure or under reduced pressure. Distillation under reduced pressure is especially economical because energy for heating can be reduced.

In the above-mentioned manner, extremely high-purity hexafluoroacetone hydrate can be obtained.

As described hereinbefore, the process of the present invention can easily produce high-purity hexafluoroacetone with little formation of by-products.

Further, high-purity hexafluoroacetone hydrate free from highly corrosive acid, etc. can be produced in a very easy manner by hydration of hexafluoroacetone and subsequent distillation.

Hexafluoroacetone and hexafluoroacetone hydrate are very useful as intermediates in the synthesis of various fluorine-containing compounds.

BEST MODE FOR CARRYING OUT THE INVENTION

The present invention is described in more detail with reference to the following Examples.

EXAMPLE 1

Spherical titanium oxide (30 g, about 30 ml) ("CS-310" produced by of Sakai Chemical Industry Co., Ltd.; particle diameter: about 3 mm) was charged into a reaction tube made of SUS316 (inner diameter: 16 mm, length: 460 mm).

The reaction tube was heated to 140° C., and hexafluoro-1,2-epoxypropane (purity: 95%, impurity content: 5% hexafluoropropene) was fed into the reaction tube under the conditions of a feed rate of 50 Nml/min and a total pressure of 3 atmospheres.

The exit gas was analyzed by gas chromatography, showing that hexafluoro-1,2-epoxypropane had not reacted. After about 2 hours, when the temperature in the reaction tube had risen to 190° C., the exit gas was analyzed again by gas chromatography, with the result that the conversion of hexafluoro-1,2-epoxypropane was almost 100% and the selectivity for hexafluoroacetone was 99% or higher.

After 3 hours of reaction, the reaction temperature was lowered to 60° C., and the exit gas was analyzed again by gas chromatography, with the result that the conversion of hexafluoro-1,2-epoxypropane was 80% and the selectivity for hexafluoroacetone was 99% or higher.

After 6 hours of reaction, the reaction temperature was raised again to 140° C., and the exit gas was analyzed. As the result, the conversion of hexafluoro-1,2-epoxypropane was almost 100% and the selectivity for hexafluoroacetone was 99% or higher.

EXAMPLE 2

Spherical titanium oxide (30 g) ("CS-310" produced by of Sakai Chemical Industry Co., Ltd.; particle diameter: about 3 mm) was charged into a reaction tube made of SUS316 (inner diameter: 16 mm, length: 460 mm).

The reaction tube was heated to 250° C., and nitrogen gas was fed into the reaction tube at a rate of 50 ml/min for 2 hours for treatment. After cooling the reaction tube to 140° C., the nitrogen gas flow was stopped, and hexafluoro-1,2-epoxypropane (purity: 95%, impurity content: 5% hexafluoropropene) was fed into the reaction tube under the conditions of a feed rate of 50 Nml/min and a total pressure of 3 atmospheres. After starting to feed hexafluoro-1,2-epoxypropane, the temperature in the reaction tube immediately rose to 190° C. The exit gas was analyzed by gas chromatography, with the result that the conversion of hexafluoro-1,2-epoxypropane was 100%. After 5 hours of reaction, the exit gas was passed into 75 g of water for 10 hours, producing 302 g of crude hexafluoroacetone hydrate. Trifluoroacetic acid, pentafluoropropionic acid and hydrofluoric acid contents were quantitatively determined by ion chromatography, with the obtained results being: $CF_3CO_2^-$, 2440 ppm; $C_2F_5CO_2^-$, 3860 ppm; and $F^-$, 805 ppm.

The produced crude hexafluoroacetone hydrate (300 g) was neutralized by addition of potassium hydrogencarbonate (2.6 g) and was subjected to distillation under reduced pressure.

The distillate fraction obtained at 85 mmHg (11.3 kPa) and 53° C. to 55° C. was 295 g of hexafluoroacetone hydrate (recovery: 98%). The hexafluoroacetone hydrate was analyzed by ion chromatography for acid, with the result that no impurities were detected except for 8 ppm of $F^-$ ions.

COMPARATIVE EXAMPLE 1

A spherical fluorinated alumina catalyst (30 g) (particle diameter: 2 to 4 mm) was charged into a reaction tube made of SUS316 (inner diameter: 16 mm, length: 460 mm). The reaction tube was heated to 140° C., and hexafluoro-1,2-epoxypropane (purity: 95%, impurity content: 5% hexafluoropropene) was fed into the reaction tube under the conditions of a feed rate of 50 Nml/min and a total pressure of 3 atmospheres. After 1 hour, the exit gas was analyzed by gas chromatography, with the result that the conversion of hexafluoro-1,2-epoxypropane was 100%. The exit gas was passed into water, producing crude hexafluoroacetone trihydrate. Trifluoroacetic acid, pentafluoropropionic acid and hydrofluoric acid contents were quantitatively determined by ion chromatography, with the obtained results being: $CF_3CO_2^-$, 1.7%; $C_2F_5CO_2^-$, 3%; and $F^-$, 1.2%.

The produced crude hexafluoroacetone trihydrate (745 g) was neutralized by addition of potassium hydrogencarbonate (91.3 g) and was subjected to distillation under reduced pressure. The distillate fraction obtained at 85 mmHg (11.3 kPa) and 53° C. to 55° C. was 554 g of hexafluoroacetone hydrate (recovery: 74%).

The residue in the still after distillation was recovered as a highly viscous liquid (219 g). An NMR analysis of the residue showed that about 50 wt. % of hexafluoroacetone remained as its monohydrate. The residue was adjusted, by addition of water, to the proportion of a trihydrate and redistilled. The distillate was water alone, with no hexafluoroacetone hydrate being recovered.

What is claimed is:

1. A process for preparing hexafluoroacetone which comprises bringing hexafluoro-1,2-epoxypropane into contact with at least one catalyst selected from the group consisting of fluorinated titanium oxide catalysts to isomerize hexafluoro-1,2-epoxypropane.

2. A process for preparing hexafluoroacetone hydrate which comprises:

bringing hexafluoro-1,2-epoxypropane into contact with at least one catalyst selected from the group consisting of titanium oxide catalysts and fluorinated titanium oxide catalysts to give hexafluoroacetone by isomerization, absorbing the produced hexafluoroacetone into water to give crude hexafluoroacetone hydrate, neutralizing the crude hexafluoroacetone hydrate with an alkali, and distilling the resulting mixture.

3. The process for preparing hexafluoroacetone hydrate according to claim 2, wherein the alkali is at least one compound selected from the group consisting of alkali metal carbonates, alkali metal hydrogencarbonates, alkali metal hydrogenphosphates, alkali metal borates, alkali metal sulfites, alkali metal hydroxides, alkaline earth metal carbonates, alkaline earth metal hydrogencarbonates, alkaline earth metal hydrogenphosphates, alkaline earth metal borates, alkaline earth metal sulfites, and alkaline earth metal hydroxides.

* * * * *